Sept. 16, 1958 F. W. ANDERSON Plant Pat. 1,751
NECTARINE TREE
Filed Jan. 31, 1958
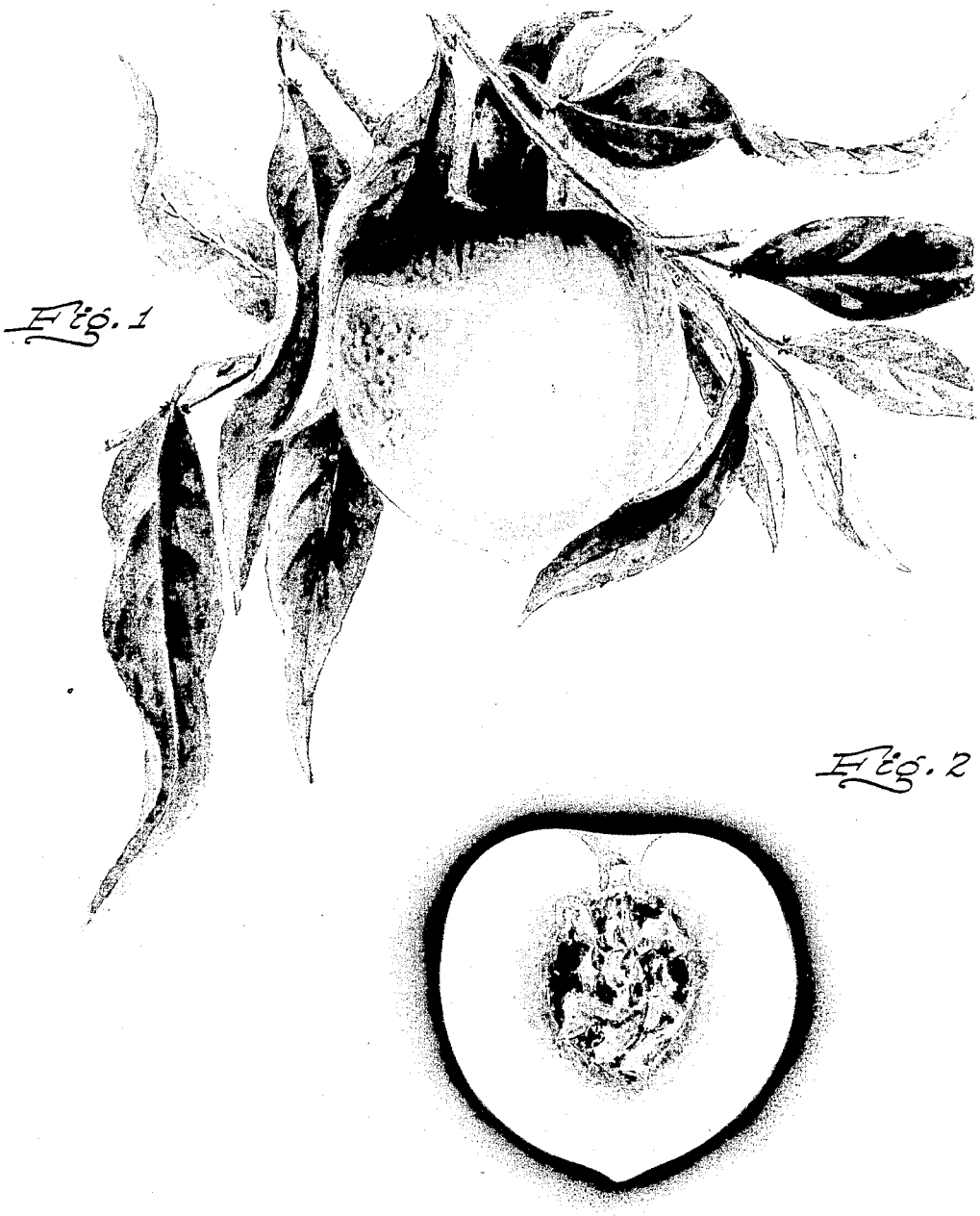
WITNESS
Addison E. Avery
INVENTOR.
Frederic W. Anderson
Webster & Webster
ATTYS.

United States Patent Office

Plant Pat. 1,751
Patented Sept. 16, 1958

1,751

NECTARINE TREE

Frederic W. Anderson, Merced, Calif., assignor to Kim Bros., Reedley, Calif., a copartnership doing business as Reedley Nursery Application January 31, 1958, Serial No. 712,600

1 Claim. (Cl. 47—62)

The present invention is directed to a new and distinct variety of nectarine tree which bears large, yellow-fleshed, clingstone fruit of generally the Le Grand type, but having a relatively late harvest period which extends the season or market availability of this type of fruit from the very last of August into early September.

As the Le Grand nectarine which I previously originated (United States Plant Patent No. 549) was, upon commercial growing, very well received in the trade, I undertook an extensive and continuing plant breeding program having—for one of its objects—the origination of other nectarine varieties bearing commercially desirable fruit of the Le Grand type, but having harvest seasons occurring at successive intervals during the summer months; this to the end that fruit of such type would be almost continuously available over a substantial period of time.

As a result of such program, and in the continuance thereof, I originated and patented the Early Le Grand (United States Plant Patent No. 980); the Red Grand (United States Plant Patent No. 1,060); the Grandeur (United States Plant Patent No. 1,265); and the Late Le Grand (United States Plant Patent No. 1,035). All of such nectarine varieties are now available on the commercial market during their respective harvest periods, and which occur at different times between the 1st week in July and the last week in August.

The present variety of nectarine tree is the latest to ripen in comparison to those mentioned above, and as it ripens—when grown in the interior valley of California—during the very last part of August and the early part of September, the market season for Le Grand type fruit is correspondingly extended.

The herein claimed nectarine tree was originated by me in my experimental orchard, located near Merced, California, by growing many hundreds of open-pollinated and crossed seedlings, and which seedlings were maintained under vary careful observation, especially as to fruit characteristics, including harvest period.

Those of such seedlings which bore commercially acceptable fruit, and which was late ripening, were top-worked onto mature trees in my experimental orchard, located as aforesaid, for the purpose of further observation. When such top-worked seedlings came into bearing, one was particularly outstanding and was selected by me for subsequent reproduction; such selected variety being the present one.

Subsequent to its origination and initial reproduction, the variety was further asexually reproduced by me, likewise by top working, in my experimental orchard, and all of said reproductions have been found to run true in all respects.

In the drawings:

Fig. 1 is an elevation showing one of the fruit, together with twigs and leaves.

Fig. 2 is a sectional elevation of one of the fruit, with the stone remaining in place.

Referring now more specifically to the pomological details of this new and distinct variety of nectarine tree, the following is an outline description; all major color plate identifications being by Maerz and Paul Dictionary of Color, except where otherwise indicated, or where common terms of color definition are employed.

Tree:
- *Size.*—Large to medium.
- *Vigor.*—Vigorous.
- *Form.*—Spreading.
- *Production.*—Very productive.
- *Bearing.*—Regular bearer.

Trunk:
- *Size.*—Stocky.

Branches:
- *Size.*—Stocky.

Leaves:
- *Size.*—Large; average length — 6⅛"; average width—1¼".
- *Margin.*—Crenate.
- *Petiole.*—Medium length.
- *Glands.*—Usually two on petiole, and two to four on blade. Alternate; reniform.
- *Stipules.*—None.
- *Color.*—Top side—medium green (22–L–8); underside—lighter green (22–J–4).

Flower buds:
- *Size.*—Medium.
- *Form.*—Obtuse.

Flowers:
- *Date of bloom.*—Midseason; i. e., medium as compared with other varieties.
- *Size.*—Large.

Fruit:
- *Maturity when described.*—Eating ripe.
- *Date of first picking.*—Average: August 30th to September 1st (September 1, 1957).
- *Date of last picking.*—Average: September 10th to 12th (September 12, 1957).
- *Size.*—Uniform; large; average diameter axially—3"; average transversely in suture plane—3".
- *Form.*—Uniform; globose.
- *Suture.*—Distinct; extends from base over entire circumference; marked depression beyond pistil point.
- *Ventral surface.*—Rounded.
- *Cavity.*—Rounded; elongated in suture plane with suture showing on both sides; average depth—9/16"; average breadth—11/16".
- *Base.*—Truncate.
- *Apex.*—Depressed.

Skin:
- *Thickness.*—Medium.
- *Texture.*—Medium.
- *Tendency to crack.*—None.
- *Down.*—Wanting.
- *Color.*—Yellow (9–L–5 to 9–K–7), partially overspread with red (3–K–11 to 4–L–10, shading darker near base to 7–L–6), with dark red mottling.

Flesh:
- *Texture.*—Firm; fine; meaty.
- *Ripens.*—Even.
- *Flavor.*—Subacid.
- *Aroma.*—Distinct.
- *Eating quality.*—Good.
- *Color.*—Yellow (9–L–4 to 9–J–7) near skin, shading lighter yellow (9–B–2) intermediate skin and stone, with purple red (6–L–1 to 6–L–6) near the stone.

Stone:

*Type.*—Cling.

*Size.*—Medium; average length—1¼"; average breadth—1⅛"; average thickness—¾".

*Form.*—Globose to oblong.

*Base.*—Straight.

*Apex.*—Rounded.

*Sides.*—Equal.

*Ridges.*—Rounded; interrupted.

*Pits.*—Elongated.

*Ventral edge.*—Thick.

*Dorsal edge.*—Full.

*Tendency to split.*—Slight.

*Color.*—Dahlia purple British Color Council Chart, #931, Sheet 178.

Use: Market; local; dessert; long distance shipping.

Shipping quality: Good.

The tree and its fruit herein described may vary in slight detail due to climatic and soil conditions under which the variety may be grown.

The following is claimed:

A new and distinct variety of nectarine tree, as illustrated and described, which bears large clingstone fruit, generally similar to the Le Grand nectarine, having yellow skin partially overspread with red; characterized essentially by a harvest period extending on the average from the last days of August to ten or twelve days into September; and further characterized by yellow flesh shading lighter from the outer to the intermediate portion, with purple red near the stone, the latter being of a purple cast.

No references cited.